United States Patent
Kaneda

(10) Patent No.: US 11,109,752 B2
(45) Date of Patent: Sep. 7, 2021

(54) DENTAL CARIES DIAGNOSIS DEVICE

(71) Applicant: NIHON UNIVERSITY, Tokyo (JP)

(72) Inventor: Takashi Kaneda, Tokyo (JP)

(73) Assignee: NIHON UNIVERSITY, Tokyo (JP)

( * ) Notice: Subject to any disclaimer, the term of this patent is extended or adjusted under 35 U.S.C. 154(b) by 57 days.

(21) Appl. No.: 16/306,985

(22) PCT Filed: Jun. 5, 2017

(86) PCT No.: PCT/JP2017/020836
§ 371 (c)(1),
(2) Date: Dec. 4, 2018

(87) PCT Pub. No.: WO2017/213091
PCT Pub. Date: Dec. 14, 2017

(65) Prior Publication Data
US 2019/0142261 A1    May 16, 2019

(30) Foreign Application Priority Data

Jun. 6, 2016   (JP) .............................. JP2016-112393

(51) Int. Cl.
*A61B 1/24* (2006.01)
*A61C 19/04* (2006.01)
(Continued)

(52) U.S. Cl.
CPC ............. *A61B 1/24* (2013.01); *A61B 1/07* (2013.01); *A61B 5/0088* (2013.01);
(Continued)

(58) Field of Classification Search
CPC ........... A61B 1/24; A61B 1/07; A61B 5/0088; A61B 1/7203; A61C 1/081; A61C 19/04
See application file for complete search history.

(56) References Cited

U.S. PATENT DOCUMENTS

| 6,561,802 B2 | 5/2003 | Alexander |
| 9,414,750 B2 | 8/2016 | Lovely |

(Continued)

FOREIGN PATENT DOCUMENTS

| JP | 2009-090091 | 4/2009 |
| JP | 2012-147909 | 8/2012 |

(Continued)

OTHER PUBLICATIONS

International Search Report dated Aug. 15, 2017, from International Application No. PCT/JP2017/020836, 4 pages.

(Continued)

*Primary Examiner* — David P Porta
*Assistant Examiner* — Mamadou Faye
(74) *Attorney, Agent, or Firm* — Meunier Carlin & Curfman LLC

(57) ABSTRACT

A dental caries diagnosis device comprising a light source which is configured to emit examination light (R) and a light receiving unit (4f) which is configured to receive the examination light (R) with which a tooth has been irradiated includes: a head-side casing (4a1) which is inserted into a mouth in a contactless manner with respect to a tooth or a gum and which projects the examination light (R) toward a tooth; and a filter (4e) which is disposed in front of the light receiving unit (4f) and which is configured to remove a noise component from the received light, wherein the light receiving unit (4f) is configured to receive the examination light (R) which has been transmitted through the tooth.

10 Claims, 5 Drawing Sheets

(51) Int. Cl.
    *A61B 1/07*   (2006.01)
    *A61B 5/00*   (2006.01)
    *A61C 1/08*   (2006.01)

(52) U.S. Cl.
    CPC ............ *A61B 5/7203* (2013.01); *A61C 1/081* (2013.01); *A61C 19/04* (2013.01)

(56) References Cited

U.S. PATENT DOCUMENTS

| | | | |
|---|---|---|---|
| 9,506,808 B2 | 11/2016 | Jeon et al. | |
| 2008/0062429 A1* | 3/2008 | Liang ................. | A61B 1/00039 356/497 |
| 2010/0112511 A1* | 5/2010 | Wu ........................ | A61B 1/247 433/31 |
| 2010/0238279 A1 | 9/2010 | Thoms et al. | |
| 2011/0117025 A1* | 5/2011 | Dacosta .................... | A61B 5/01 424/9.6 |
| 2013/0071808 A1 | 3/2013 | Van der Laan | |
| 2013/0189641 A1* | 7/2013 | Perfect ............... | A61B 1/00089 433/29 |
| 2015/0250572 A1 | 9/2015 | Gramann et al. | |
| 2015/0305627 A1* | 10/2015 | Islam ................... | A61B 5/0022 433/27 |

FOREIGN PATENT DOCUMENTS

| | | |
|---|---|---|
| WO | 2005/013843 | 2/2005 |
| WO | 2007067776 | 6/2007 |
| WO | 2012002564 A1 | 1/2012 |

OTHER PUBLICATIONS

International Preliminary Report on Patentability [English] dated May 15, 2018, from International Application No. PCT/JP2017/020836, 10 pages.

Instructions for use, DIAGNOcam 2170 (version 8), KaVo Dental GmbH [online], Apr. 22, 2014.

Kawashima, Y. et al. "Clinical Science Course, Usefulness for Dental Caries Features and Clinical Dentistry in Latest Dental Caries Detection Imagae Examination Device Without Exposure to X-rays 'KaVO DIAGNOcam", The Nippon Dental Review, Jan. 2014, pp. 107-112 [English].

Extended European Search Report relating to European Application No. 17810266.1, dated Jan. 17, 2020.

* cited by examiner

DENTAL CARIES DIAGNOSIS DEVICE

TECHNICAL FIELD

The present invention relates to a dental caries diagnosis device.

Priority is claimed on Japanese Patent Application No. 2016-112393, filed Jun. 6, 2016, the content of which is incorporated herein by reference.

BACKGROUND ART

For example, Non-Patent Document 1 discloses a dental caries detection image examination device using laser light. The dental caries detection image examination device in Non-Patent Document 1 irradiates a tooth with the laser light, receives the laser light reflected by the tooth, and detects a dental caries from an intensity of the received laser light. Such a dental caries detection image examination device has a structure in which a tooth is surrounded by a laser light irradiation unit using a clip and a noise component due to external light at the time of examining is prevented from entering a light receiving unit.

CITATION LIST

Patent Literature

[Non-Patent Document 1]
Yuusuke KAWASHIMA and three others. "Clinical Science Course. Usefulness for Dental Caries Features and Clinical Dentistry in Latest Dental Caries Detection Image Examination Device Without Exposure to X-rays 'KaVO DIAGNOcam.'" The Nippon Dental Review, January 2014, Reprint, p. 107 to 112

SUMMARY OF INVENTION

Technical Problem

However, when a dental caries detection image examination device such as that described in Non-Patent Document 1 is used, a laser light irradiation unit is fixed to the gum in the mouth. Thus, a testee whose gum is in contact with the laser light irradiation unit during the examination is likely to feel uncomfortable.

The present invention was made in view of the above-described problems, and an objective of the present invention is to provide a dental caries diagnosis device that does not cause a testee discomfort.

Solution to Problem

A dental caries diagnosis device according to an aspect of the present invention is a dental caries diagnosis device which includes a light source which is configured to emit examination light and a light receiving unit which is configured to receive the examination light with which a tooth has been irradiated including: a head portion which is inserted into a mouth without coming in contact with a tooth or a gum and which projects the examination light toward a tooth; and a filter which is disposed in front of the light receiving unit and which is configured to remove a noise component from the received light, wherein the light receiving unit is configured to receive the examination light which has been transmitted through the tooth.

In the dental caries diagnosis device according to the aspect, the light source may be a light emitting diode.

The dental caries diagnosis device according to the aspect may include: a prism or a mirror which is configured to refract the examination light with which the tooth has been irradiated toward the light receiving unit.

The dental caries diagnosis device according to the aspect may include: a light amount adjustment unit which is configured to adjust the amount of the examination light.

In the dental caries diagnosis device according to the aspect, the head portion may include: side wall portions which have a tooth accommodation space and are disposed to face each other so that the side wall portions surround the accommodation space; and a light irradiation unit which is configured to irradiate the examination light from the side wall portions toward a tooth.

Advantageous Effects of Invention

According to the present invention, a head portion is inserted into a mouth without coming in contact with a testee's gingiva (gum). For this reason, the testee does not feel uncomfortable. Here, since the head portion is away from a testee's tooth, external light enters the inside of the head portion through a gap between the head portion and the gum and light received by a light receiving unit includes a noise component such as the external light in addition to examination light. In order to remove the noise component other than the examination light from the light received by the light receiving unit, a filter is provided in front of the light receiving unit in the present invention. Thus, an inspector who makes a diagnosis can capture a clear diagnostic image of a dental caries using the head portion that is not in contact with the gum.

DESCRIPTION OF EMBODIMENTS

In the following drawings, in order to set each member to have a distinguishable size, the scale of each member is appropriately changed.

First Embodiment

Figure 1:
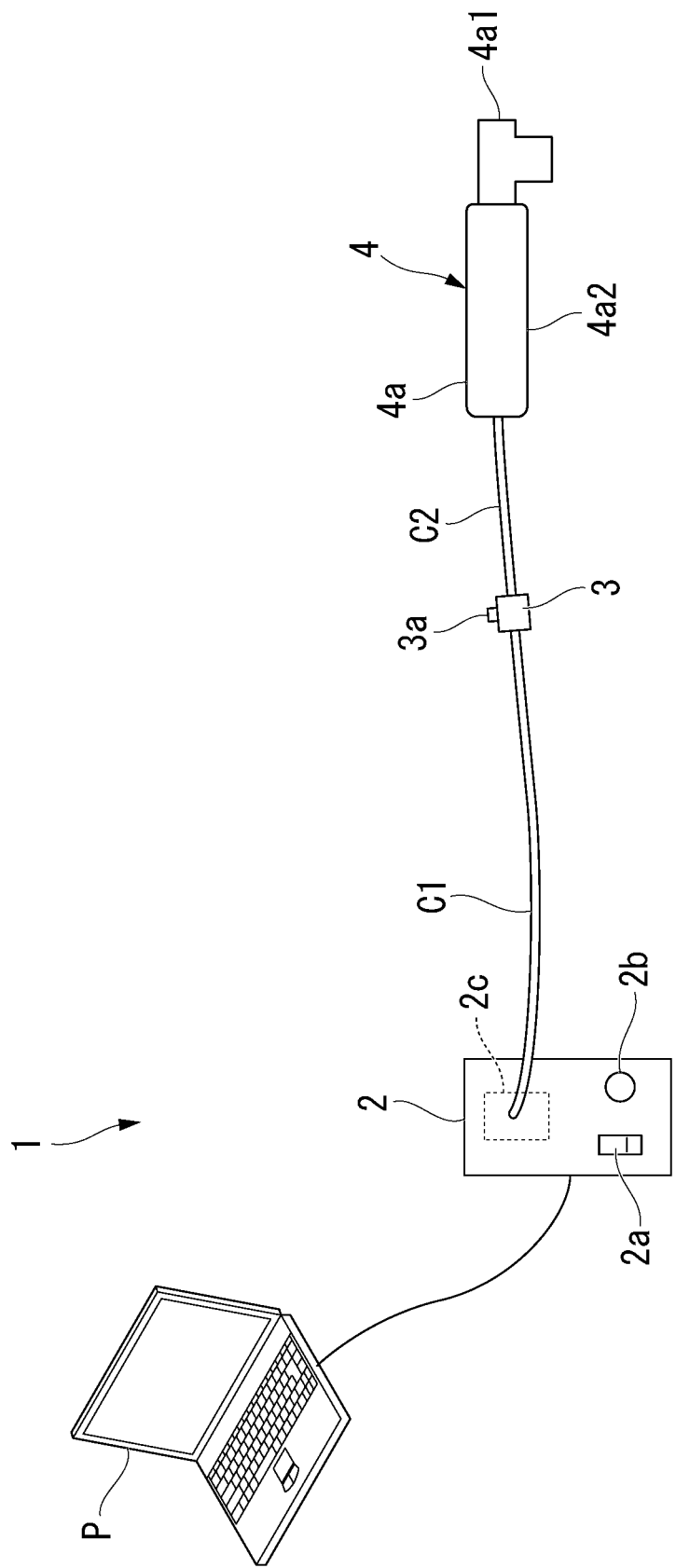
FIG. 1 is a device constitution diagram of a dental caries diagnosis device according to an embodiment of the present invention.

Embodiments of a dental caries diagnosis device associated with the present invention will be described below with reference to the drawings. FIG. 1 is a device constitution diagram of a dental caries diagnosis device 1 according to this embodiment.

The dental caries diagnosis device 1 according to this embodiment includes a main body portion 2, a shutter unit 3, and a handpiece 4, the main body portion 2 and the shutter unit 3 are connected to each other through a cable C1, and the shutter unit 3 and the handpiece 4 are connected to each other through a cable C2. The main body portion 2 is a device configured to supply light to the handpiece 4 and transmit and receive signals to and from a computer P and receives supplied electric power when connected to an electric power strip or the like. The main body portion 2 includes an electric power switch 2a, a light amount adjustment unit 2b, and a light source 2c.

The electric power switch 2a is a switch configured to switch between supply start and supply stop of a power supply. The light amount adjustment unit 2b is a knob configured to adjust an amount of light of a light irradiation unit 4b which will be described later in the handpiece 4 and can adjust an amount of light of the light source stepwise or steplessly. The main body portion 2 is connected to the shutter unit 3 through the cable C1 having an optical fiber light guide connected to the light source installed therein. The main body portion 2 is connected to the computer P through a USB cable. The computer P includes a monitor which displays a video from a camera 4f which will be described later. The light source 2c is a light emitting diode (LED) with a central wavelength of 780 nm configured to emit examination light R and can an amount of light thereof can be adjusted through adjustment of the light amount adjustment unit 2b.

The shutter unit 3 is connected to the main body portion 2 via the cable C1 and is connected to the handpiece 4 via the cable C2 having the optical fiber light guide installed therein. The shutter unit 3 is an apparatus which includes a shutter switch 3a and performs a shutter operation of the camera 4f which will be described later in the handpiece 4. An inspector can acquire a still image or a moving image through the camera 4f by pressing down the shutter switch 3a.

Figure 2A:
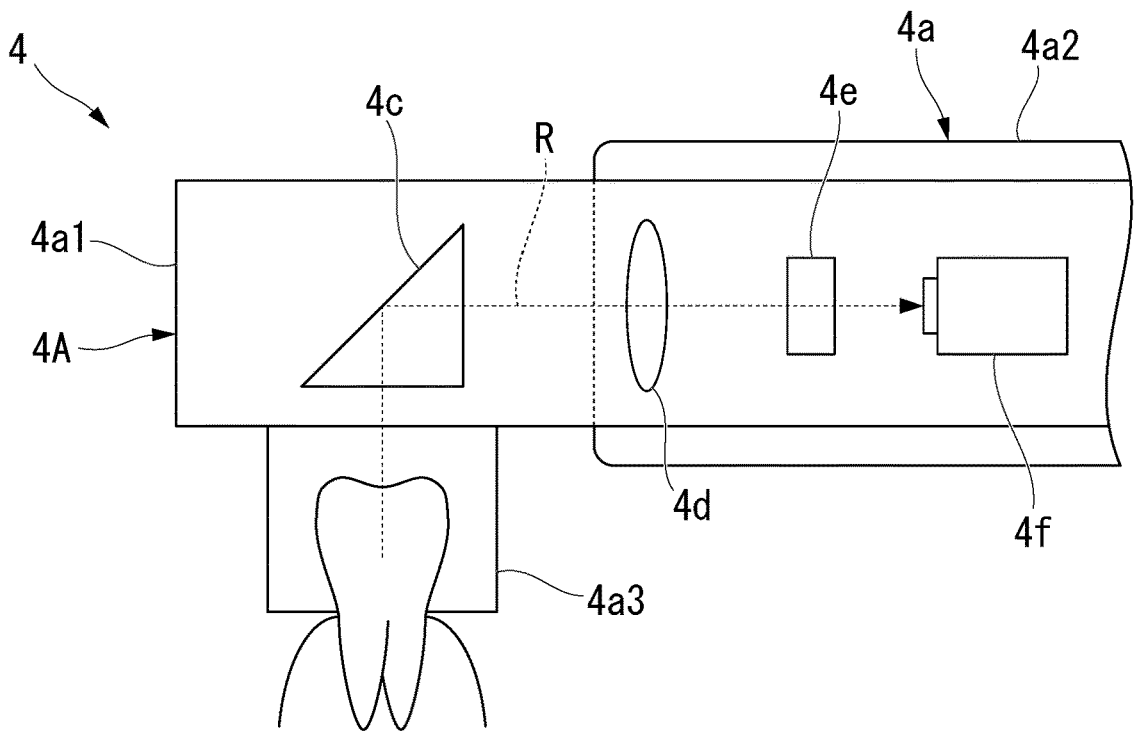
FIG. 2A is a side cross-sectional view of a handpiece in the dental caries diagnosis device according to the embodiment of the present invention.
Figure 2B:
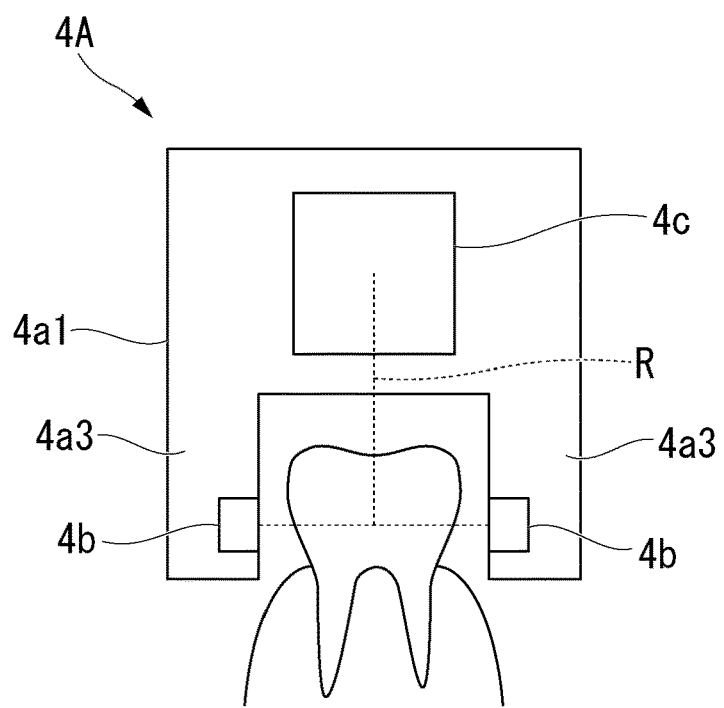
FIG. 2B is a front view of a head portion in the handpiece of the dental caries diagnosis device according to the embodiment of the present invention.

FIG. 2A is a side cross-sectional view of the handpiece 4 in the dental caries diagnosis device 1 according to this embodiment. FIG. 2B is a front view of a head portion 4A in the handpiece 4 of the dental caries diagnosis device 1 according to this embodiment. As shown in FIGS. 2A and 2B, the handpiece 4 includes a casing 4a, the light irradiation unit 4b, a prism 4c, a lens 4d, a cut filter 4e, and the camera 4f (light receiving unit).

The casing 4a is an elongated member and includes a head-side casing 4a1 and a grasp portion 4a2 which is shown in FIG. 1. The casing 4a has a hollow or translucent member formed therein through which the examination light R irradiated from the light irradiation unit 4b can pass.

The head-side casing 4a1 is a resin part inserted into a testee's mouth and has the light irradiation unit 4b and the prism 4c embedded therein. As shown in FIG. 2, the head-side casing 4a1 has an accommodation space formed to accommodate a tooth between two side wall portions 4a3 erected in parallel at intervals from a distal end of a substantially tubular member through the two side wall portions 4a3. The width of the two side wall portions 4a3 is set wider than an average value of widths of adult molar teeth. In the head-side casing 4a1, a part of the side wall portions 4a3 is formed of a translucent member and the light irradiation unit 4b is embedded in a translucent portion of the side wall portions 4a3. Such a head-side casing 4a1 is inserted into the testee's mouth such that a tooth is sandwiched between the two side wall portions 4a3. The head-side casing 4a1 can be detached from the grasp portion 4a2.

The grasp portion 4a2 is a portion by which the inspector grasps the handpiece 4 in a range not including the head-side casing 4a1 and has the head-side casing 4a1 attached thereto. The lens 4d, the cut filter 4e, and the camera 4f are provided inside the grasp portion 4a2.

The light irradiation unit 4b is embedded in each of the two side wall portions 4a3 in the head-side casing 4a1 and irradiates examination light R from the sides of a tooth root portion inserted into a concave portion. The light irradiation units 4b are connected to the light source of the main body portion 2 via the cables C1 and C2 having the optical fiber light guides. The prism 4c is embedded in a bottom portion of the concave portion in the head-side casing 4a1. The prism 4c is a member configured to refract examination light R which is irradiated from the light irradiation unit 4b and passes through the testee's a tooth at 90 degrees toward the camera 4f.

The head portion 4A is constituted of the head-side casing 4a1 and the light irradiation unit 4b and the prism 4c provided inside the head-side casing 4a1. The head portion 4A is inserted into the mouth without coming in contact with a tooth or a gum and projects examination light R toward the tooth. The head portion 4A can be detached and the inspector can use the head portion 4A according to a size of the testee's tooth.

The lens 4d is a part configured to cause examination light R refracted through the prism 4c to converge and is provided inside the casing 4a. The cut filter 4e is provided behind the lens 4d and in front of the camera 4f so that examination light R passing through the lens 4d passes therethrough. The cut filter 4e is a device configured to remove external light (a noise component) from a fluorescent lamp from light passing through the lens 4d and passes only examination light R with a wavelength of 780 nm.

The camera 4f is a complementary metal-oxide semiconductor (CMOS) sensor configured to receive light passing through the cut filter 4e and can capture an image and a moving image. The camera 4f receives a signal from the shutter unit 3 and captures an image. The camera 4f transmits the image and the moving image to the main body portion 2 via the cable C2 and the cable C1. The captured image and moving image are transmitted from the main body portion 2 to the computer P via a USB cable and can be observed on the monitor of the computer P in real time.

An operation of such a dental caries diagnosis device 1 according to this embodiment will be described.

The inspector first presses the electric power switch 2a. Thus, the light source is turned on, and examination light R is transmitted to the light irradiation unit 4b via the optical fiber light guides of the cable C1 and the cable C2. The inspector inserts the head-side casing 4a1 of the handpiece 4 into the testee's mouth and keeps the head-side casing 4a1 out of contact with the testee's tooth. The examination light R irradiated from the light irradiation unit 4b is incident on the testee's tooth from the side. When the examination light R is applied to the testee's tooth, the inspector operates the light amount adjustment unit 2b in accordance with a texture and a size of the testee's tooth, a portion of the tooth to be examined, and the like and adjusts the amount of light.

The examination light R incident on the testee's tooth is refracted and scattered inside the testee's tooth and a part of the examination light R is incident on the prism 4c from above. At that time, since the testee's mouth is open, the external light from the fluorescent lamp is incident on the prism together with the examination light R. The examination light R incident on the prism 4c is reflected toward the lens 4d and converges through the lens 4d. The examination light R passing through the lens 4d passes through the cut filter 4e. Thus, the external light passing through the lens 4d together with the examination light R is shielded and only the examination light R reaches the camera 4f.

The inspector can observe the examination light R received by the camera 4f on the monitor or the like of the computer P in real time. The inspector operates the shutter unit 3 and can acquire the examination light R received by the camera 4f as an image and a moving image. The inspector detects a dental caries generated inside the testee's tooth from the acquired image.

According to such a dental caries diagnosis device 1 according to this embodiment, the inspector can use the head-side casing 4a1 in a state in which the head-side casing 4a1 is not in contact with a tooth or a gum. Thus, the testee does not feel the discomfort of the head-side casing 4a1 coming in contact with a gum. Therefore, the inspector can smoothly diagnose a dental caries. In order to prevent the examination light R received by the camera 4f from mixing with external light when the head-side casing 4a1 is not brought into contact with a tooth or a gum, the cut filter 4e is provided. Thus, there is hardly any noise in an image acquired by the dental caries diagnosis device 1 and it is possible to maintain diagnostic accuracy of the inspector regardless of an external environment.

The dental caries diagnosis device 1 according to this embodiment may use an LED as the light source. Thus, the present invention is easy to handle and a size of the entire device can be reduced as compared with the case in which laser light is used for the dental caries diagnosis device in the related art.

In the dental caries diagnosis device 1 according to this embodiment, the handpiece 4 includes the prism 4c configured to refract the examination light R toward the camera 4f. Thus, it is unnecessary to provide the camera 4f in the head-side casing 4a1 to receive the examination light R which has been transmitted through the testee's tooth. Therefore, even in this case, it is possible to reduce a size of the head portion 4A inserted into the testee's mouth and the testee becomes less likely to cause discomfort.

The dental caries diagnosis device 1 according to this embodiment can adjust the light amount adjustment unit 2b to adjust an amount of light of the light source in the main body portion 2. Therefore, the inspector can perform a diagnosis without scattering the examination light R by adjusting an amount of light of the light source, for example, even with a tooth that has high translucency like an infant tooth or a front tooth.

In the dental caries diagnosis device 1 according to this embodiment, the LED with the central wavelength of 780 nm is used as the light source. This is based on the fact that light of a general indoor fluorescent lamp includes little light with a wavelength of 780 nm. Thus, the cut filter 4e can easily exclude external light from the fluorescent lamp incident together with the examination light R by excluding light other than the light with a wavelength of 780 nm.

With the dental caries diagnosis device 1 according to this embodiment, teeth with various sizes can be coped with by replacing the head portion 4A with a head portion 4A having a different width of a concave portion. Therefore, it is possible to observe an infant tooth, a front tooth, and the like that are difficult to observe using the dental caries examination device of the related art.

Second Embodiment

Figure 3:
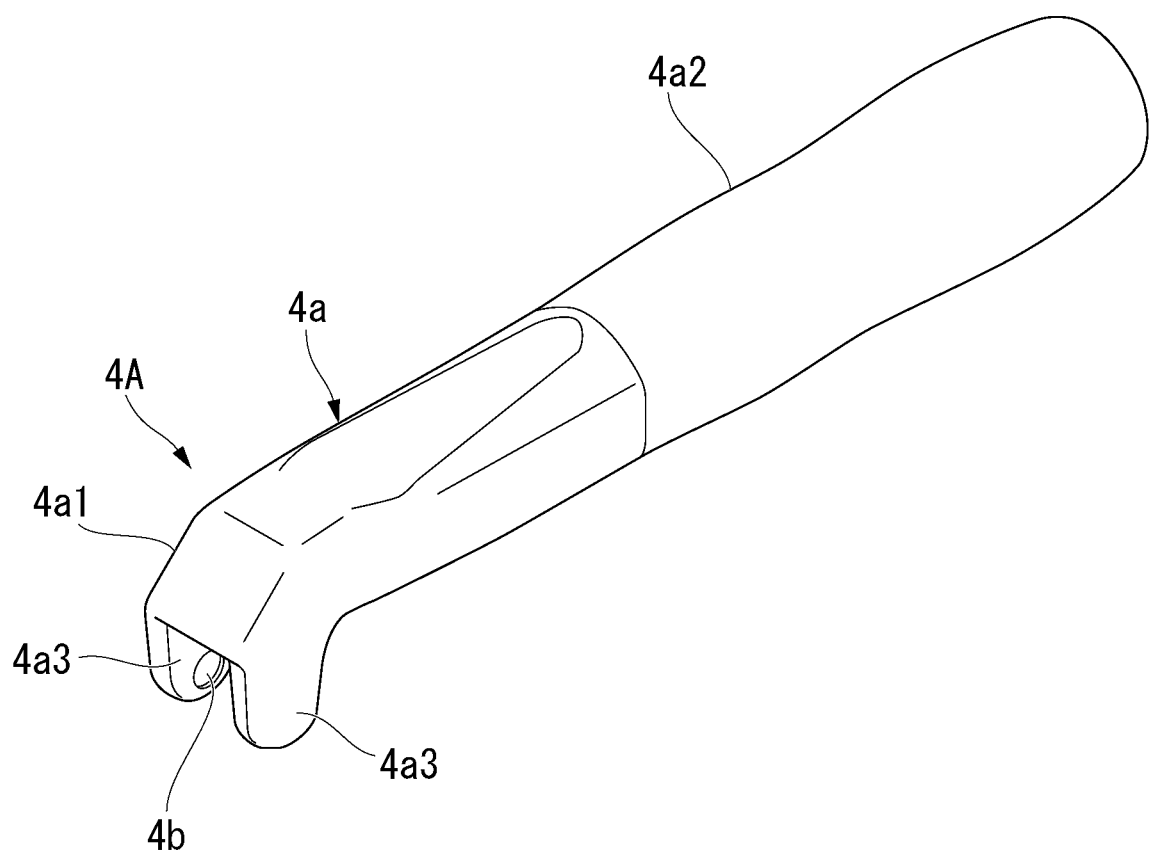
FIG. 3 is a perspective view of a handpiece in a modified example of the dental caries diagnosis device according to the embodiment of the present invention.
Figure 4:
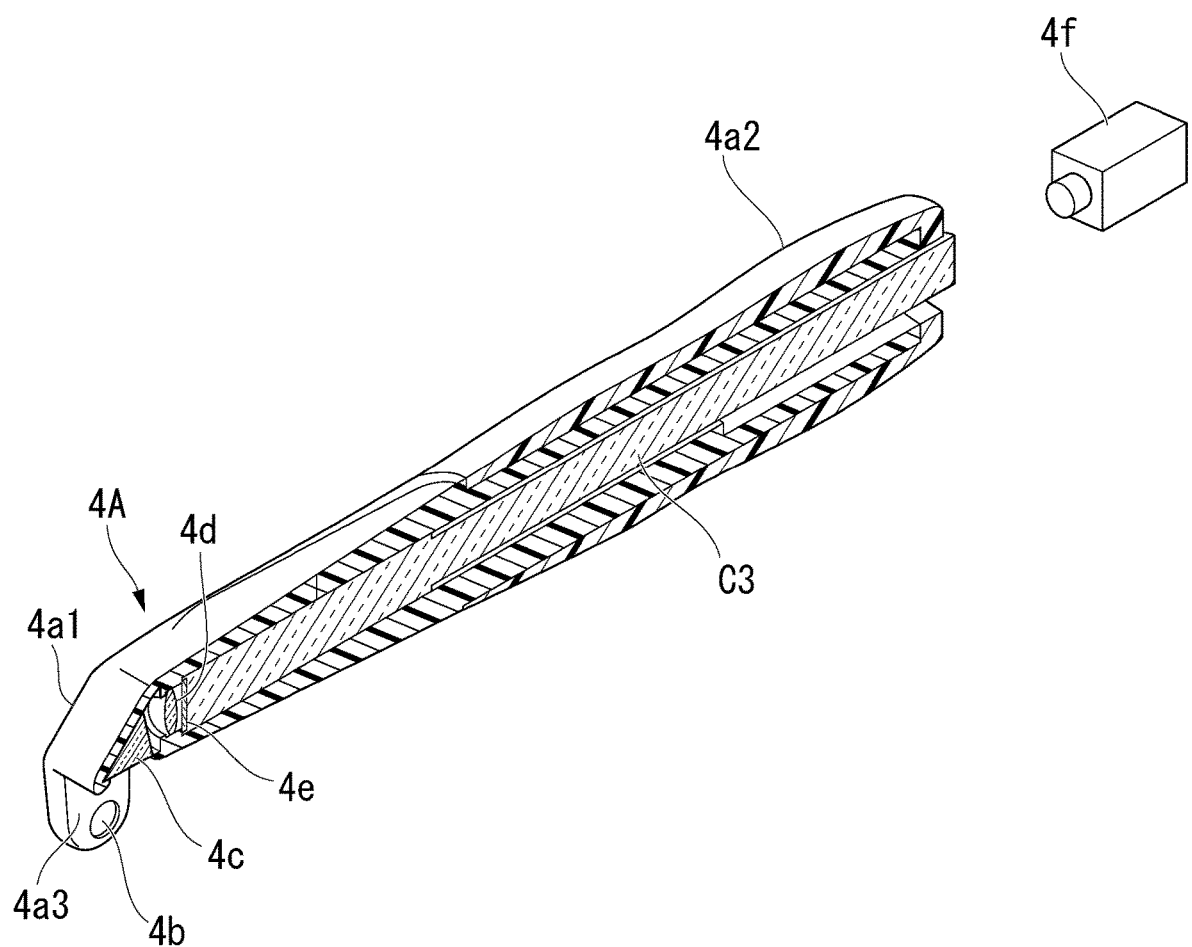
FIG. 4 is a side cross-sectional view of a handpiece in the modified example of the dental caries diagnosis device according to the embodiment of the present invention.

FIG. 3 is a perspective view of a handpiece 4 in a modified example of the dental caries diagnosis device 1 according to this embodiment. FIG. 4 is a side cross-sectional view of the handpiece 4 in the modified example of the dental caries diagnosis device 1 according to this embodiment. A second embodiment of the dental caries diagnosis device 1 will be described with reference to FIGS. 3 and 4. It should be noted that constituent elements that are the same as the first embodiment will be denoted with the same reference numerals and a description thereof will be omitted.

In a dental caries diagnosis device 1 in this embodiment, a handpiece 4 does not include a camera 4f. As shown in FIG. 4, the cable C3 which is a bundle of optical fibers is accommodated inside a grasp portion 4a2. In an end portion of a head-side casing 4a1 in the handpiece 4 in this embodiment, side wall portions 4a3 provided to sandwich an accommodation space of a tooth have end portions formed in a curved surface shape. Furthermore, the camera 4f is connected to a cable C3 exposed from the handpiece 4 and receives examination light R transmitted through the cable C3.

According to such a dental caries diagnosis device 1 according to this embodiment, as in the first embodiment, the inspector can use the head-side casing 4a1 in a state in which the head-side casing 4a1 is in non-contact with the tooth or the gum. Thus, the testee does not feel uncomfortable due to the head-side casing 4a1 in contact with a gum. Therefore, the inspector can smoothly diagnose a dental caries. In order to prevent the examination light R received by the camera 4f from mixing with external light when the head-side casing 4a1 is brought into non-contact with the tooth or the gum, a cut filter 4e is provided. Thus, noise is hardly present in an image acquired by the dental caries diagnosis device 1 and it is possible to maintain diagnostic accuracy of the inspector regardless of an external environment.

Also, according to the dental caries diagnosis device 1 in this embodiment, when an end portion of the side wall portions 4a3 in the head-side casing 4a1 is formed in a curved surface shape and is inserted into the testee's mouth, the testee does not feel pain even when the side wall portion 4a3 touches the testee.

Third Embodiment

Figure 5:
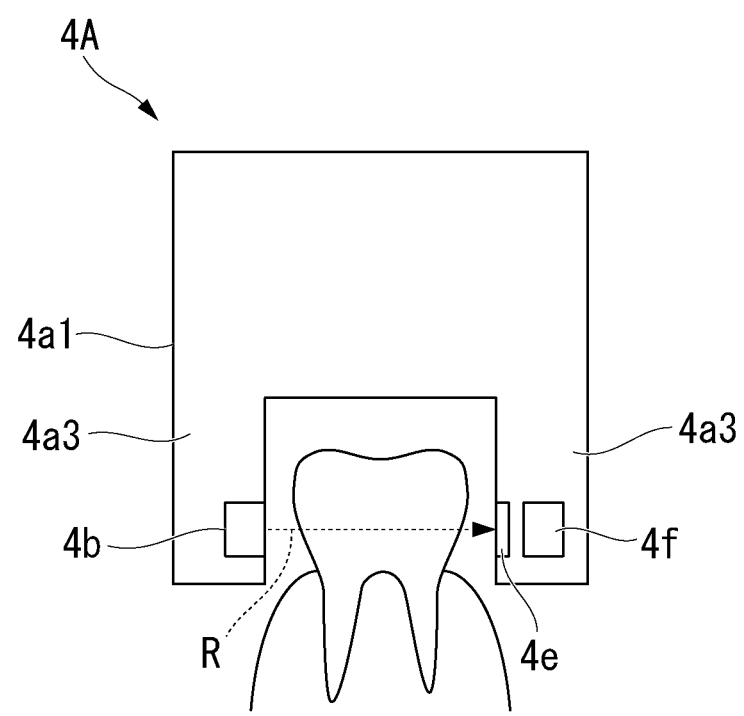
FIG. 5 is a front view of a head portion of a handpiece in a modified example of the dental caries diagnosis device according to the embodiment of the present invention.

FIG. 5 is a front view of a head portion 4A of a handpiece 4 in a modified example of the dental caries diagnosis device 1 according to this embodiment. A third embodiment of the dental caries diagnosis device 1 will be described with reference to FIG. 5. It should be noted that constituent elements that are the same as the first embodiment will be denoted with the same reference numerals and a description thereof will be omitted.

As shown in FIG. 5, in a dental caries diagnosis device 1 in this embodiment, a head portion 4A does not include a prism 4c and includes a cut filter 4e and a camera 4f. A light irradiation unit 4b is installed on one of side wall portions 4a3s provided to sandwich a concave accommodation portion of a head-side casing 4a1 and the cut filter 4c and the camera 4f are installed on a side wall portion 4a3 and a side wall portion 4a3 facing the side wall portion 4a3. Examination light R irradiated from the light irradiation unit 4b is transmitted through the testee's tooth and is incident on the camera 4f disposed opposite to the light irradiation unit 4b.

According to such as dental caries diagnosis device 1 associated with this embodiment, as in the first embodiment, the inspector can use the head-side casing 4a1 in a state in which the head-side casing 4a1 is in non-contact with a tooth or a gum. Thus, the testee does not feel uncomfortable due to the head-side casing 4a1 in contact with a gum. Therefore, the inspector can smoothly diagnose a dental caries. In order to prevent examination light R received by the camera 4f from mixing with external light when the head-side casing 4a1 is brought into con-contact with a tooth or a gum, the cut filter 4e is provided. Thus, a noise is hardly present in an image acquired by the dental caries diagnosis device 1 and it is possible to maintain diagnostic accuracy of the inspector regardless of the external environment.

According to this embodiment, since a distance between the light irradiation unit 4b and the camera 4f is shorter than that in the first embodiment, it is possible to diagnose a dental caries on the basis of high-intensity examination light R. Therefore, the inspector can obtain a higher-accuracy image from the camera 4f and it is possible to further improve dental caries diagnostic accuracy.

The present invention is not limited to the above-described embodiments, and for example, the following modified examples are conceivable.

(1) Although the main body portion 2 and the computer P are connected through the USB cable in the above-described embodiments, the present invention is not limited thereto. The main body portion 2 and the computer P may be connected by radio. The main body portion 2 may be connected to, for example, a tablet or the like.

(2) Although the shutter unit 3 is provided as a separate member from the main body portion 2 and the handpiece 4 in the above-described embodiment, the present invention is not limited thereto. The shutter unit 3 may be provided in the main body portion 2 or the handpiece 4. In this case, since a device constitution can be simplified, it is easy to carry the dental caries diagnosis device 1.

(3) Although the handpiece 4 includes the prism 4c in the first embodiment, the present invention is not limited thereto. The handpiece 4 may include a mirror and reflect light which has been transmitted through the testee's tooth toward the camera 4f using the mirror.

INDUSTRIAL APPLICABILITY

The present invention can be used for a dental caries diagnosis device

REFERENCE SIGNS LIST

1 Dental caries diagnosis device
2 Main body portion
2a Electric power switch
2b Light amount adjustment unit
3 Shutter unit
3a Shutter switch
4 Handpiece
4A Head portion
4a3 Side wall portion
4b Light irradiation unit
4c Prism
4e Cut filter
4f Camera (light receiving unit)

What is claimed is:

1. A dental caries diagnosis device, comprising:
a light source configured to emit examination light;
a head portion which is inserted into a mouth without coming in contact with a tooth or a gum, projects the examination light toward a tooth, and is attachable and detachable;
a light receiving unit configured to receive the examination light with which the tooth has been irradiated; and
a filter which is disposed in front of the light receiving unit and which is configured to remove a noise component from a received light,
wherein the light receiving unit is connected to a cable which is exposed from the head portion and through which light passes,
the light source is connected to the head portion by an optical fiber light guide,
the head portion includes
a pair of side wall portions having a tooth accommodation space and disposed to face each other such that the side wall portions surround the accommodation space, and
a pair of termination points for the optical fiber light guide connected to the light source provided in the pair of side wall portions and configured to irradiate the examination light toward each other and to the tooth, and
the light receiving unit receives the examination light that has been transmitted through the tooth in a direction different from a facing direction of the pair of termination points for the optical fiber light guide and has gone out thereof.

2. The dental caries diagnosis device according to claim 1, wherein the light source is a light emitting diode.

3. The dental caries diagnosis device according to claim 1, comprising a prism or a mirror which is configured to refract the examination light with which the tooth has been irradiated toward the light receiving unit.

4. The dental caries diagnosis device according to claim 1, comprising a light amount adjustment unit which is configured to adjust an amount of the examination light.

5. The dental caries diagnosis device according to claim 2, comprising a prism or a mirror which is configured to refract the examination light with which the tooth has been irradiated to the light receiving unit.

6. The dental caries diagnosis device according to claim 5, comprising a light amount adjustment unit which is configured to adjust an amount of the examination light.

7. The dental caries diagnosis device according to claim 2, comprising a light amount adjustment unit which is configured to adjust an amount of the examination light.

8. The dental caries diagnosis device according to claim 3, comprising a light amount adjustment unit which is configured to adjust an amount of the examination light.

9. The dental caries diagnosis device according to claim 1, comprising a shutter portion which is formed as a separate member from the head portion and in which an operation for acquiring a still image is performed.

10. The dental caries diagnosis device according to claim 1, wherein the noise component light is a light from a fluorescent lamp.

* * * * *